United States Patent
Chmielewski

[11] Patent Number: 5,891,120
[45] Date of Patent: Apr. 6, 1999

[54] ABSORBENT ARTICLE COMPRISING TOPSHEET, BACKSHEET AND ABSORBENT CORE WITH LIQUID TRANSFERRING LAYER NEAR BACKSHEET

[75] Inventor: Harry J. Chmielewski, Norcross, Ga.

[73] Assignee: Paragon Trade Brands, Inc., Norcross, Ga.

[21] Appl. No.: 872,628

[22] Filed: Jun. 9, 1997

Related U.S. Application Data

[63] Continuation of Ser. No. 791,257, Jan. 30, 1997, abandoned.

[51] Int. Cl.$^6$ ..................................................... A61F 13/15
[52] U.S. Cl. ........................ 604/378; 604/368; 604/372; 604/369
[58] Field of Search ................................... 604/358, 367, 604/368, 369, 372, 378, 385.1

[56] References Cited

U.S. PATENT DOCUMENTS

| | | |
|---|---|---|
| Re. 32,649 | 4/1988 | Brandt et al. . |
| 4,585,448 | 4/1986 | Enloe . |
| 4,610,678 | 9/1986 | Weisman et al. . |
| 4,673,402 | 6/1987 | Weisman et al. . |
| 4,685,915 | 8/1987 | Hasse et al. . |
| 4,695,278 | 9/1987 | Lawson . |
| 4,699,619 | 10/1987 | Bernardin . |
| 4,699,823 | 10/1987 | Kellenberger et al. . |
| 4,761,258 | 8/1988 | Enloe . |
| 4,764,325 | 8/1988 | Angstadt . |
| 4,765,780 | 8/1988 | Angstadt . |
| 4,795,454 | 1/1989 | Dragoo . |
| 4,798,603 | 1/1989 | Meyer et al. . |
| 4,834,735 | 5/1989 | Alemany et al. . |
| 4,846,823 | 7/1989 | Enloe . |
| 4,888,231 | 12/1989 | Anstadt . |
| 4,988,344 | 1/1991 | Reising et al. . |
| 5,037,409 | 8/1991 | Chen et al. . |
| 5,047,023 | 9/1991 | Berg . |
| 5,061,259 | 10/1991 | Goldman et al. . |
| 5,147,343 | 9/1992 | Kellenberger . |
| 5,149,335 | 9/1992 | Kellenberger et al. . |
| 5,156,902 | 10/1992 | Pieper et al. . |
| 5,356,403 | 10/1994 | Faulks et al. . |
| 5,364,382 | 11/1994 | Latimer et al. . |
| 5,403,301 | 4/1995 | Huffman et al. ...................... 604/385.2 |
| 5,429,629 | 7/1995 | Latimer et al. . |
| 5,486,166 | 1/1996 | Bishop et al. . |
| 5,490,846 | 2/1996 | Ellis et al. . |
| 5,520,673 | 5/1996 | Yarbrough et al. ...................... 604/378 |
| 5,525,407 | 6/1996 | Yang . |
| 5,562,650 | 10/1996 | Everett et al. ........................... 604/378 |

*Primary Examiner*—John G. Weiss
*Assistant Examiner*—Dennis Ruhl
*Attorney, Agent, or Firm*—Hunton & Williams

[57] ABSTRACT

In an absorbent article comprising a liquid-permeable topsheet, a liquid-impermeable backsheet, and an absorbent structure positioned between the topsheet and the backsheet, the absorbent structure includes an upper layer, a lower layer, and an elongate, absorbent core, which is formed from cellulosic fibers and from distributed particles of a superabsorbent polymer (SAP) and which has an elongate, central portion with an absorbency under load (AUL) not less than about 12 grams/gram. The absorbent core has a front end, a back end, and two ears projecting from the elongate, central portion, near the front end with the superabsorbent polymer (SAP) at an upper surface in essentially no concentration and at each of the ears in a concentration that is about one half of the concentration along the elongate, central portion. Being formed from polyester, polyolefinic, cellulosic, conjugate, or mixed fibers, the upper layer is capable of absorbing some of a liquid permeating the upper layer from the topsheet and of transferring to the upper surface of the absorbent core some of the liquid permeating the upper layer from the topsheet. Having a basis weight not more than about 150 grams per square meter and an absorbency under load (AUL) not more than about 6 grams/gram, the lower layer has a minimal absorbency but is capable of transferring to a lower surface of the absorbent core a liquid permeating the lower layer from the absorbent core.

20 Claims, 1 Drawing Sheet

ABSORBENT ARTICLE COMPRISING TOPSHEET, BACKSHEET AND ABSORBENT CORE WITH LIQUID TRANSFERRING LAYER NEAR BACKSHEET

This is a continuation, of application Ser. No. 08/791,257, filed Jan. 30, 1997 now abandoned.

TECHNICAL FIELD OF THE INVENTION

This invention pertains to an absorbent article, such as a disposable diaper, which comprises a topsheet, a backsheet, and an absorbent core having a liquid-transferring layer near the backsheet for enhanced absorptive efficiency of the absorbent core.

BACKGROUND OF THE INVENTION

Commonly, an absorbent article, such as a disposable diaper or an adult incontinent garment, comprises a liquid-permeable topsheet, a liquid-impermeable backsheet, and an absorbent core formed from cellulosic fibers, which typically are comminuted softwood pulp fibers, and from distributed particles of a superabsorbent polymer (SAP) with the absorbent core positioned between the topsheet and the backsheet. It is known to provide the absorbent article with one or more other layers formed from cellulosic fibers or other materials to perform various liquid-absorbing, liquid-distributing, and cushioning functions.

Thus, it is known to position an upper layer formed from cellulosic fibers between the topsheet and an upper surface of the absorbent core. The upper layer absorbs some of a liquid permeating the upper layer from the topsheet. Also, the upper layer transfers the rest of the liquid to the upper surface of the absorbent core, primarily through a wicking action. Such an upper layer positioned between the topsheet and the absorbent core is known also as a wicking layer, a transfer layer, or an acquisition layer.

Also, it is known to wrap the absorbent core of such an absorbent article with one or more layers formed from cellulosic fibers, such as one or more tissue layers. Generally, each wrapping layer is capable of absorbing a quantity of a liquid permeating such wrapping layer.

This invention has resulted from ongoing efforts to improve an absorbent article having a liquid-permeable topsheet, a liquid-impermeable backsheet, and an absorbent core, as discussed above, so as to enhance the liquid-storing efficiency of the absorbent core.

SUMMARY OF THE INVENTION

This invention has resulted from a realization that an absorbent article having a liquid-permeable topsheet, a liquid-impermeable backsheet, and an absorbent core, as discussed above, can be more efficiently used to store a liquid, such as urine, if the absorbent structure is provided with a lower layer having a limited capability to absorb the liquid permeating the lower layer from the absorbent core but having an enhanced capability for transferring the liquid permeating the lower layer from the absorbent core to a lower surface of the absorbent core.

This invention provides an absorbent article comprising a liquid-permeable topsheet, a liquid-impermeable backsheet, and an absorbent structure, which is positioned between the topsheet and the backsheet and which includes an absorbent core. The absorbent structure further includes a lower layer, which has a minimal absorbency but which provides means for transferring a liquid permeating the lower layer from the absorbent core to the lower surface of the absorbent core. Specifically, this invention contemplates that the lower layer has a basis weight not more than about 150 grams per square meter and an absorbency under load (AUL) not more than about 6 grams/gram.

Moreover, the absorbent structure may include an upper layer, as known in prior absorbent articles. If included, the upper layer provides means for absorbing some of a liquid permeating the upper layer from the topsheet and for transferring to the upper surface of the absorbent core the rest of the liquid permeating the upper layer from the topsheet. This invention is operative whether or not an upper layer is included.

So that the absorbent core has sufficient absorbency to take good advantage of this invention, this invention contemplates that the absorbent core is formed from cellulosic fibers and from distributed particles of a superabsorbent polymer (SAP) so as to have an elongate, central portion with an absorbency under load (AUL) not less than about 12 grams/gram.

In a preferred embodiment, the absorbent core has a front end, a back end, and two ears projecting from the elongate, central portion, near the front end. In the preferred embodiment, the superabsorbent polymer (SAP) is present at the upper surface in essentially no concentration and at each of the ears in a concentration about one half of the concentration of the superabsorbent polymer (SAP) along the elongate, central portion.

If the lower layer is formed from cellulosic fibers, the basis weight of the lower layer must be suitably selected so that the lower layer has a limited capability to absorb the liquid permeating the lower layer from the absorbent core, but so that the lower layer has an enhanced capability for transferring the liquid permeating the lower layer from the absorbent core to a lower surface of the absorbent core.

Desirably, the absorbent core has a comparatively higher density, which is in a range from about 0.12 grams per cubic centimeter to about 0.22 grams per cubic centimeter. Desirably, the lower layer when formed from cellulosic fibers has a comparatively lower density, which is in a range from about 0.06 grams per cubic centimeter to about 0.12 grams per cubic centimeter.

Preferably, the lower layer is an air-laid pulp layer having a basis weight of about 105 grams per square meter or a folded, three-ply, air-laid pulp layer, each ply having a basis weight of about 35 grams per square meter. Alternatively, the lower layer is a folded, three-ply, tissue layer, either embossed or unembossed, each ply having a basis weight of about 37 grams per square meter.

In an alternative configuration contemplated by this invention, each of the upper and lower layers is a tissue layer having a basis weight of about 16 grams per square meter. In other alternatives, the lower layer is a non-woven web made from cellulosic, synthetic polymeric, or synthetic conjugate fibers or mixtures of such fibers or from an open-celled, synthetic polymeric foam.

Preferably, so as to stabilize the absorbent core, the lower layer has a wet strength not less than about 0.04 kilonewtons per meter (kN/m) in the cross or machine direction and the upper and lower layers extend beyond and are attached to each other at one or both of such ends.

These and other objects, features, and advantages of this invention are evident from the following description of a preferred embodiment of this invention, with reference to the accompanying drawings.

DETAILED DESCRIPTION OF THE PREFERRED EMBODIMENT

Figure 1:
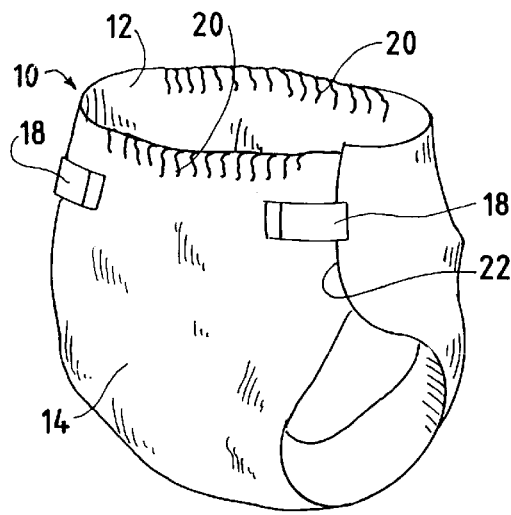
FIG. 1 is a fragmentary, perspective view of a disposable diaper exemplifying an absorbent article according to this invention, in an assembled condition.
Figure 2:
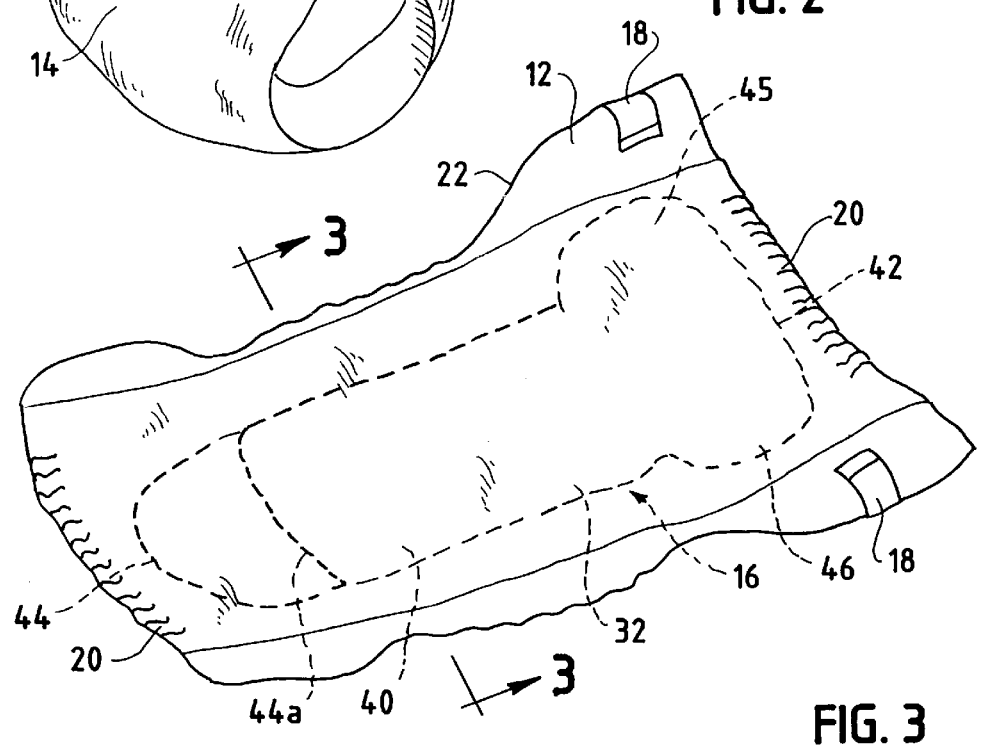
FIG. 2 is a fragmentary, perspective view of the disposable diaper of FIG. 1, in a flattened condition.
Figure 3:
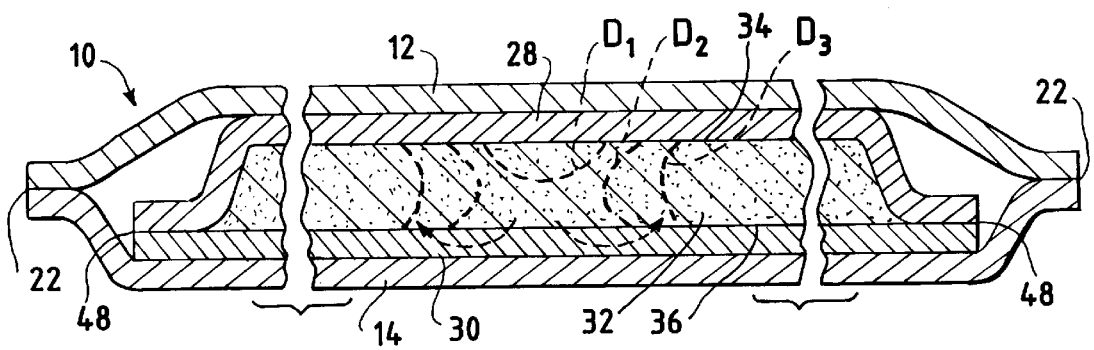
FIG. 3 is a fragmentary, sectional view taken along line 3—3 of FIG. 2, in a direction indicated by arrows.

As shown in FIGS. 1, 2, and 3, a disposable diaper 10 constitutes a preferred embodiment of this invention. According to this invention, the disposable diaper 10 can store a liquid, such as urine, with enhanced efficiency.

The disposable diaper 10 may be appropriately sized for infant use or for adult use. If sized for adult use, the disposable diaper 10 may be also called an incontinent garment. It may be here noted that this invention may be also embodied in a wound dressing or another absorbent article other than a disposable diaper.

Broadly, the disposable diaper 10 comprises a liquid-permeable topsheet 12 of a known type, a liquid-impermeable backsheet 14 of a known type, and an absorbent structure 16 positioned between the topsheet 12 and the backsheet 14. The disposable diaper 10 has tape fasteners 18 of a known type, elasticized waistbands 20 of a known type, and other known features outside the scope of this invention. The topsheet 12 and the backsheet 14 are bonded adhesively around outer edges 22 of the disposable diaper 10, in a known manner, so as to encapsulate the absorbent structure 16. The topsheet 12, which may be also called a facing sheet, may be made from a non-woven web of cellulosic fibers, synthetic polymeric fibers, or blends of cellulosic and synthetic polymeric fibers and may be apertured. The backsheet 14 may be made from a synthetic polymeric film, such as a polyethylene film. Details of the topsheet 12 and the back sheet 14 are outside the scope of this invention.

Except as illustrated and described herein, the disposable diaper 10 may be substantially similar to the disposable diaper disclosed in Huffman et al. U.S. Pat. No. 5,403,301, the disclosure of which is incorporated herein by reference.

In the preferred embodiment, the absorbent structure 16 includes an upper layer 28 near the topsheet 12, a lower layer 30 near the backsheet 14, and an absorbent core 32 positioned between the upper layer 18 and the lower layer 30. As shown in FIG. 3, the absorbent core 32 has an upper surface 34 near the upper layer 18 and a lower surface 36 near the lower layer 30. As shown in FIG. 2, the absorbent core 32 has an elongate, central portion 40 with a front end 42 and a back end 44, along with two ears 46 near the front end 44. In an alternative embodiment (not shown) the upper layer 28 is omitted.

The upper layer 28 provides means for absorbing some of a liquid, such as urine, that permeates the upper layer 28 from the topsheet 12 and for transferring to the upper surface 34 of the absorbent core 32 the rest of the liquid that permeates the upper layer 28 from the topsheet 12. Preferably, the upper layer 28 is made a non-woven web, either carded or through-air-bonded, as made from polyester (polyethylene terephthalate) fibers, polyolefinic, or synthetic conjugate fibers or mixtures of such fibers, with a basis weight of about 40 grams per square meter, and with a width of about 76 millimeters.

Alternatively, the upper layer 28 is a tissue layer formed from cellulosic fibers with a basis weight of about 16 grams per square meter, with a width of about 90 millimeters, and with a length sufficient to cover the absorbent core 32 over the full length of the absorbent core 32. In an alternative embodiment (not shown) wherein the upper layer is a nonwoven web, as noted above, the upper layer 28 has a length sufficient to cover a part but not all of the length of the absorbent core.

The absorbent core 32 is formed in a known manner, as by a pocket-forming process, from cellulosic fibers, such as wood pulp, and from distributed particles of a superabsorbent polymer (SAP) of a known type. Preferred for the superabsorbent polymer (SAP) is Hoechst-Celenese IM-4510 surface cross-linked superabsorbent polyacrylate, which is available commercially from Hoechst-Celenese of Portsmouth, Va.

In the preferred embodiment, about 10 grams of softwood pulp and about 7 grams of the superabsorbent polymer (SAP) are used to form the absorbent core 32 so as to have a surface layer of softwood pulp with a basis weight of about 40 grams per square meter at the upper surface 34, so as to have a density in a range from about 0.12 grams per cubic centimeter to about 0.22 grams per cubic centimeter, preferably a density of about 0.17 grams per cubic centimeter, so as to have a basis weight of about 800 grams per square meter along the elongate, central portion 40, and so as to have an absorbency under load (AUL) not less than about 12 grams/gram along the elongate, central portion 40. Generally, because of manufacturing variables, the absorbency under load (AUL) of such an absorbent core is controllable with an accuracy of about ±3 grams/gram.

In the preferred embodiment, the absorbent core 32 is formed so that the superabsorbent polymer (SAP) is present at essentially no concentration at the surface layer at the upper surface 34, at a concentration sufficient to achieve the absorbency under load (AUL) noted above along the elongate, central portion, and at each of the ears 46 at a concentration that is one half of the concentration of the superabsorbent polymer (SAP) along the elongate, central portion 40.

According to this invention, the lower layer 30 has a minimal capacity to store a liquid but provides means for transferring a liquid, such as urine, that permeates the lower layer 30 from the absorbent core 32 to the lower surface 36 of the absorbent core 32. Specifically, this invention contemplates that the lower layer 30 has an absorbency under load (AUL) not more than about 6 grams/gram. Generally, because of manufacturing variables, the absorbency under load (AUL) of such a lower layer is controllable with an accuracy of about ±1 gram/gram. Although the lower layer 30 may exhibit a wicking action, a wicking action is not necessary.

Desirably, if the lower layer 30 is formed from cellulosic fibers, the lower layer 30 has a density in a range from about 0.06 grams per cubic centimeter to about 0.12 grams per cubic centimeter, preferably a density of about 0.08 grams per cubic centimeter. As compared to the previously discussed, comparatively higher density of the absorbent core 32, the lower layer 30 has a comparatively lower density.

For purposes of this invention, the absorbency under load (AUL) of an absorbent product refers to the amount of synthetic urine absorbed by several target samples of the absorbent product, if each target sample in a sample holder is immersed in synthetic urine, while such target sample is subjected to a pressure of about 0.5 psi (713.2 grams per square meter) for a swelling time of about 10 minutes, and if each target sample and its sample holder then are drained for about 60 seconds.

Several target samples are used for each absorbent product, each target sample being is cut from such absorbent product via a two-inch diameter die. For each absorbent product, the mean average of the absorbencies under load (AUL) for the target samples cut from such absorbent product is taken as the absorbency under load (AUL) for such absorbent product.

For purposes of this invention, synthetic urine is prepared pursuant to included directions from Synthetic Urine Concentrate, Catalog No. 8362, which is available commercially from Ricca Chemical Co. of Portsmouth, Va. An aqueous solution of one percent by weight of sodium chloride may be alternatively used as synthetic urine. Several sample holders are used, one for each target sample, each sample holder having a known weight within an accuracy of about ±0.03 gram is used. Several weights are used, one for each target sample, each weight being designed to apply a pressure of 713.2 grams (±0.03 grams) per square meter. A balance having an accuracy of ±0.01 gram is used.

For each target sample, the absorbency under load (AUL) is calculated by subtracting the dry weight of such target sample and its sample holder from the wet weight thereof, after such target sample and its sample holder have been immersed in synthetic urine, while such target sample was subjected to a pressure of about 0.5 psi (713.2 grams per square meter) for a swelling time of about 10 minutes, and then have been drained for about 60 seconds.

A first configuration contemplated by this invention for the lower layer 30 is a folded, three-ply, air-laid layer of wood pulp with each ply having a basis weight of about 35 grams per square meter, with each ply having a density of about 0.08 grams per cubic centimeter, with a total weight of about 4 grams, with the folded layer having a folded width of about 90 millimeters and a length sufficient to cover the full length of the absorbent core 32, and with an absorbency under load (AUL) of about 6 grams/gram.

A second configuration contemplated by this invention for the lower layer 30 is a folded, three-ply, tissue layer formed from cellulosic fibers, either embossed or unembossed, with each ply having a basis weight of about 37 grams per square meter, with each ply having a density of about 0.08 grams per cubic centimeter, with a total weight of about 4 grams, with the folded layer having a folded width of about 90 millimeters and a length sufficient to cover the full length of the absorbent core 32, and with an absorbency under load (AUL) of about 6 grams/gram.

A third configuration contemplated by this invention for the lower layer 30 is a single layer formed from air-laid, cellulosic fibers with a basis weight of about 105 grams per square meter, with a density of about 0.08 grams per cubic centimeter, with a width of about 90 millimeters, and with an overall length greater than the overall length of the absorbent core 32.

When any of the first, second, and third configurations noted above is used for the lower layer 30, the lower layer 30 has a wet strength not less than about 0.04 kilonewtons per meter (kN/m) of width in the cross or machine direction. For purposes of this invention, the wet strength of the lower layer 30 is measured by TAPPI Test Method T 494, "Tensile breaking properties of paper and paperboard (using constant rate of elongation apparatus)", and by TAPPI Test Method T 456, "Wet tensile breaking strength of paper and paperboard".

A fourth configuration contemplated by this invention for the lower layer 30 is a single tissue layer formed from cellulosic fibers with a basis weight of about 16 grams per square meter, with a width of about 90 millimeters, and with an overall length greater than the overall length of the absorbent core 32.

A non-woven web of cellulosic, synthetic polymeric, or synthetic conjugate fibers or mixtures of such fibers or a sheet of open-celled, synthetic polymeric foam may be alternatively employed for the lower layer 30, so long as its absorbency under load (AUL) does not exceed about 6 grams/gram.

The upper layer 28 is applied over the absorbent core 32 but is not bonded to the absorbent core 32. The lower layer 30 is bonded adhesively to the absorbent core 32 by a hot-melt adhesive, which preferably is applied via two spiral-spray nozzles over the full length of the absorbent core 32, with an adhesive add-on of about 0.05 milligrams per centimeter of length of the absorbent core 32. The upper layer 28 is bonded adhesively to the lower layer 30, at outer edges 48 surrounding the absorbent core 32, preferably via a hot-melt adhesive applied in a continuous line. The lower layer 30 is bonded adhesively to the backsheet 14, along the disposable diaper 10, preferably via a hot-melt adhesive applied in continuous lines.

In FIG. 3, broken lines $D_1$, $D_2$, and $D_3$ respectively represent regions of the absorbent core 32 that are wetted by a liquid, such as urine, which is transferred by the upper layer 28 to the upper surface 34 of the absorbent core 32. As suggested by curved arrows in FIG. 3, any liquid that permeates the absorbent core 32 is transported by the lower layer 30 to the lower surface 36 of the absorbent core 32, which thus is rewetted by the liquid transported by the lower layer 30.

Because this invention enables the absorbent core 32 to store a liquid, such as urine, with enhanced efficiency, the absorbent core 32 may have an overall length that is about 40% to about 80% less than the overall length of the lower layer 32, so as to extend along a front portion of the lower layer 32 and so as to terminate at a back edge 44a indicated by a broken line in FIG. 1, without significant reduction in its effective capacity to store such a liquid but with concomitant reductions not only in the diaper cost but also in the bulkiness of the disposable diaper 10.

Figure 4:
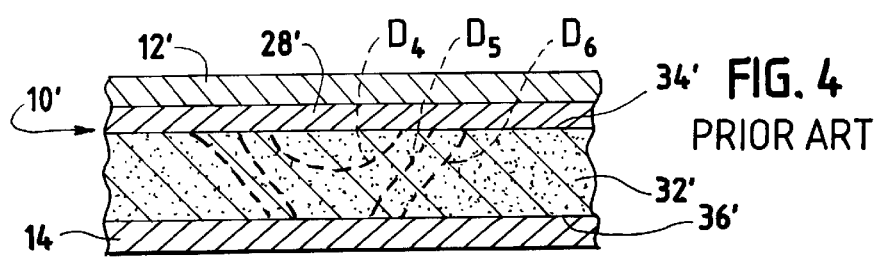
FIG. 4 is an analogous, fragmentary, sectional view taken through an absorbent article according to prior art.

In FIG. 4, in which reference numbers with primes are used to refer to elements that may be similar to elements referenced by similar numbers without primes in FIGS. 1, 2, and 3, a disposable diaper 10' according to prior art is illustrated. The disposable diaper 10' has a topsheet 12' similar to the topsheet similar to the topsheet 12, a backsheet 14' similar to the backsheet 14, and an absorbent structure, which includes an upper layer 28' similar to the upper layer 28, which includes an absorbent core 32' similar to the absorbent core 32, but which does not include a lower layer similar to the lower layer 30.

In FIG. 4, broken lines $D_4$, $D_5$, and $D_6$ respectively represent regions of the absorbent core 32' that are wetted by a liquid, such as urine, which is transferred by the upper layer 28 to the upper surface 34' of the absorbent core 32'. The disposable diaper 10' does not have any means to transport any liquid permeating the absorbent core 32' to the lower surface 36' of the absorbent core 32' so as to rewet the absorbent core 32'.

If the disposable diaper 10' were provided at the lower surface 36' of the absorbent core 32' with a lower layer (not shown) having an absorbency under load (AUL) that would be substantially more than about 6 grams/gram, the lower layer would be less effective for rewetting the lower surface 36' of the absorbent core 32', when compared to the effectiveness of the lower layer 30 of the absorbent core 32 for rewetting the lower surface 36 of the absorbent core 32 in the preferred embodiment.

Various modifications may be made in the preferred embodiment without departing from the scope and spirit of this invention.

I claim:

1. An absorbent article comprising a liquid-permeable topsheet, a liquid-impermeable backsheet, and an absorbent structure positioned between the topsheet and the backsheet, the absorbent structure including a lower layer near the backsheet and an absorbent core positioned above the lower layer, the absorbent core being formed from cellulosic fibers and from distributed particles of a superabsorbent polymer (SAP) and having an elongate, central portion with an absorbency under load (AUL) not less than about 12 grams/gram, the absorbent core having an upper surface facing the top sheet and a lower surface facing the backsheet, the lower layer providing means for transferring a liquid permeating the lower layer from the absorbent core to the lower surface of the absorbent core, the lower layer having a basis weight not more than about 150 grams per square meter and having an absorbency under load (AUL) not more than about 6 grams/gram.

2. The absorbent article of claim 1 wherein the lower layer has an overall length and wherein the absorbent core extends along a front portion of the lower layer and has an overall length that is about 40% to about 80% less than the overall length of the lower layer.

3. The absorbent article of claim 1 wherein the lower layer is formed from cellulosic fibers, wherein the absorbent core has a density in a range from about 0.12 grams per cubic centimeter to about 0.22 grams per cubic centimeter, and wherein the lower layer has a density in a range from about 0.06 grams per cubic centimeter to about 0.12 grams per cubic centimeter.

4. An absorbent article comprising a liquid-permeable topsheet, a liquid-impermeable backsheet, and an absorbent structure positioned between the topsheet and the backsheet, the absorbent structure including an upper layer near the topsheet, a lower layer near the backsheet, and an absorbent core positioned between the upper and lower layers, the absorbent core being formed from cellulosic fibers and from distributed particles of a superabsorbent polymer (SAP) and having an elongate, central portion with an absorbency under load (AUL) not less than about 12 grams/gram, the absorbent core having an upper surface facing the topsheet and a lower surface facing the backsheet, the upper layer providing means for absorbing some of a liquid permeating the upper layer from the topsheet and for transferring to the upper surface of the absorbent core the rest of the liquid permeating the upper layer from the topsheet, the lower layer providing means for transferring a liquid permeating the lower layer from the absorbent core to the lower surface of the absorbent core, the lower layer having a basis weight not more than about 150 grams per square meter and having an absorbency under load (AUL) not more than about 6 grams/gram.

5. The absorbent article of claim 4 wherein the lower layer has an overall length and wherein the absorbent core extends along a front portion of the lower layer and has an overall length that is about 40% to about 80% less than the overall length of the lower layer.

6. The absorbent article of claim 4 wherein the lower layer is formed from cellulosic fibers, wherein the absorbent core has a density in a range from about 0.12 grams per cubic centimeter to about 0.22 grams per cubic centimeter, and wherein the lower layer has a density in a range from about 0.06 grams per cubic centimeter to about 0.12 grams per cubic centimeter.

7. The absorbent article of claim 6 wherein, so as to stabilize the absorbent core, the lower layer has a wet strength not less than about 0.04 kilonewtons per meter (kN/m) of width in the cross or machine direction and the upper and lower layers extend beyond and are attached to each other at one or both of the front and back ends of the absorbent core.

8. The absorbent article of claim 7 wherein the upper and lower layers of the absorbent structure are attached to each other at both of the front and back ends of the absorbent core.

9. The absorbent article of claim 4 wherein each of the upper and lower layers of the absorbent structure is a tissue layer having a basis weight of about 16 grams per square meter.

10. An absorbent article comprising a liquid-permeable topsheet, a liquid-impermeable backsheet, and an absorbent structure positioned between the topsheet and the backsheet, the absorbent structure including an upper layer near the topsheet, a lower layer near the backsheet, and an absorbent core positioned between the upper and lower layers, the absorbent core having a front end and a back end, the absorbent core being formed from cellulosic fibers and from distributed particles of a superabsorbent polymer (SAP) and having a density in a range from about 0.12 grams per cubic centimeter to about 0.22 grams per cubic centimeter, the absorbent core having an elongate, central portion with an absorbency under load (AUL) not less than about 12 grams/gram, the absorbent core having an upper surface facing the topsheet and a lower surface facing the backsheet, the upper layer being formed from fibers selected from polyester, polyolefinic, cellulosic, and synthetic conjugate fibers and mixtures of such fibers and providing means for absorbing some of a liquid permeating the upper layer from the topsheet and for transferring to the upper surface of the absorbent core the rest of the liquid permeating the upper layer from the topsheet, the lower layer providing means for transferring a liquid permeating the lower layer from the absorbent core to the lower surface of the absorbent core, the lower layer having a wet strength not less than about 0.04 kilonewtons per meter (kN/m) in the cross or machine direction and the upper and lower layers extending beyond and being attached to each other at one or both of the front and back ends of the absorbent core so as to stabilize the absorbent core, the lower layer having a basis weight not more than about 150 grams per square meter and having an absorbency under load (AUL) not more than about 6 grams/gram, the lower layer having an overall length and the absorbent core extending along a front portion of the lower layer and having an overall length that is about 40% to about 80% less than the overall length of the lower layer, whereby the absorbent core functions as the principal liquid-storage layer of the absorbent article.

11. The absorbent article of claim 10 wherein the upper and lower layers of the absorbent structure are attached to each other at both of the front and back ends of the absorbent core.

12. The absorbent article of claim 10 wherein the absorbent core has a front end, a back end, and two ears projecting from the elongate, central portion, near the front end, the superabsorbent polymer (SAP) being present at the upper surface in essentially no concentration and at each of the ears in a concentration about one half of the concentration of the superabsorbent polymer (SAP) along the elongate, central portion.

13. The absorbent article of claim 10 wherein the lower layer is formed from cellulosic fibers and has a density in a range from about 0.06 grams per cubic centimeter to about 0.12 grams per cubic centimeter.

14. The absorbent article of claim 13 wherein the lower layer of the absorbent structure is an air-laid pulp layer having a basis weight of about 105 grams per square meter.

15. The absorbent article of claim 13 wherein the lower layer of the absorbent structure is a folded, three-ply, air-laid pulp layer, each ply having a basis weight of about 35 grams per square meter.

16. The absorbent article of claim 13 wherein the lower layer of the absorbent structure is a folded, three-ply, embossed tissue layer, each ply having a basis weight of about 37 grams per square meter.

17. The absorbent article of claim 13 wherein the lower layer of the absorbent structure is a folded, multiple-ply, unembossed tissue layer, each ply having a basis weight of about 37 grams per square meter.

18. The absorbent article of claim 10 wherein each of the upper and lower layers of the absorbent structure is a tissue layer having a basis weight of about 16 grams per square meter.

19. The absorbent article of claim 10 wherein the lower layer of the absorbent structure is a non-woven web made from cellulosic, synthetic polymeric, or synthetic conjugate fibers or mixtures of such fibers.

20. The absorbent article of claim 10 wherein the lower layer of the absorbent structure is made from an open-celled, synthetic polymeric foam.

* * * * *